(12) United States Patent
MacDonald

(10) Patent No.: US 9,820,027 B2
(45) Date of Patent: Nov. 14, 2017

(54) SWEAT PROOF EARPHONES

(71) Applicant: Gregory Michael MacDonald, Alameda, CA (US)

(72) Inventor: Gregory Michael MacDonald, Alameda, CA (US)

(*) Notice: Subject to any disclaimer, the term of this patent is extended or adjusted under 35 U.S.C. 154(b) by 0 days.

(21) Appl. No.: 14/927,463

(22) Filed: Oct. 30, 2015

(65) Prior Publication Data

US 2016/0127817 A1    May 5, 2016

Related U.S. Application Data

(60) Provisional application No. 62/073,024, filed on Oct. 31, 2014.

(51) Int. Cl.
*H04R 1/10* (2006.01)
*A61M 1/00* (2006.01)
*A61F 11/00* (2006.01)
*H04R 1/34* (2006.01)

(52) U.S. Cl.
CPC ......... *H04R 1/1016* (2013.01); *A61M 1/0023* (2013.01); *A61F 11/006* (2013.01); *H04R 1/345* (2013.01); *H04R 2225/63* (2013.01); *H04R 2460/11* (2013.01)

(58) Field of Classification Search
CPC ............... H04R 1/1016; H04R 1/1091; H04R 2201/10; H04R 1/1058; H04R 1/105; H04R 1/10; H04R 1/02; H04R 1/1066; H04R 1/1075; H04R 2460/11; H04R 25/652; H04R 1/1008; H04R 2225/025; H04R 2460/09; H04R 25/658; H04R 5/033; H04R 25/65; H04R 2460/00; H04R 2460/13; H04R 5/0335; H04R 2225/63; H04R 1/345; A61M 1/008; A61M 1/0023; A61F 11/002; A61F 11/008; A61F 11/006
USPC .................................................. 381/380, 328
See application file for complete search history.

(56) References Cited

U.S. PATENT DOCUMENTS

| 2,729,974 A | * | 1/1956 | Lee ......................... G01M 9/04 73/147 |
| 5,868,139 A | * | 2/1999 | Zeece, Sr. ............... A61F 11/08 128/864 |
| 6,059,803 A | * | 5/2000 | Spilman .............. A61M 1/0023 604/319 |

(Continued)

FOREIGN PATENT DOCUMENTS

| JP | 2007143087 | * | 6/2007 | ............... H04R 1/10 |
| JP | 2007143087 A | * | 6/2007 | ............... H04R 1/10 |

*Primary Examiner* — Davetta Q Goins
*Assistant Examiner* — Oyesola C Ojo
(74) *Attorney, Agent, or Firm* — Gregory M. MacDonald, Esq.

(57) ABSTRACT

The present invention provides a device for removing sweat from the inner ear by creating a vacuum in connecting tubing between the inner ear and a converging-diverging nozzle. When air enters the front of the converging-diverging nozzle, its velocity accelerates as it flows through the smaller cross-sectional area in the middle section, which causes a drop in pressure in the middle section and a resulting vacuum in the connecting tubing. This vacuum draws sweat from the bottom of the inner ear toward the middle of the converging-diverging nozzle, where it drips out of either end, resulting in sweat being removed from the inner ear.

4 Claims, 5 Drawing Sheets

(56) References Cited

U.S. PATENT DOCUMENTS

| | | | |
|---|---|---|---|
| 6,406,484 B1* | 6/2002 | Lang | A61B 90/10 |
| | | | 600/417 |
| 6,991,638 B2* | 1/2006 | Wang | A61M 1/0023 |
| | | | 606/162 |
| 8,638,970 B2 | 1/2014 | Burton | |
| 2007/0100300 A1* | 5/2007 | Hashemian | A61F 11/002 |
| | | | 604/275 |
| 2007/0152355 A1* | 7/2007 | Hartley | B01F 5/0413 |
| | | | 261/76 |
| 2008/0183125 A1* | 7/2008 | Issa | A61F 11/006 |
| | | | 604/26 |
| 2012/0140967 A1* | 6/2012 | Aubert | H04R 25/456 |
| | | | 381/325 |
| 2013/0038831 A1* | 2/2013 | Dillard | G02C 11/10 |
| | | | 351/158 |
| 2013/0327087 A1 | 12/2013 | Nadolny | |
| 2014/0211959 A1 | 7/2014 | Boyajian | |

* cited by examiner

SWEAT PROOF EARPHONES

CROSS-REFERENCE TO RELATED APPLICATIONS

This application claims the benefit of U.S. Provisional Application Ser. No. 62/073,024, filed Oct. 31, 2014, the entire contents of which is hereby incorporated herein by reference for all purposes as if fully set forth herein, under 35 U.S.C. 119(e).

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

SEQUENCE LISTING

Not Applicable

BACKGROUND OF INVENTION

1. Field of the Invention

The present invention relates to headphones for listening to audio, and more particularly to earphones, which remain inserted in the ear when sweat is present.

2. Description of Related Art

Earphones, which are also known as earbuds, earpods, or in-ear headphones, are miniature headphones that are inserted into the ear, to allow a user to privately listen to music from a smartphone, MP3 player, or similar electronic device. Earphones are lightweight and compact, making it easy for users to wear them while performing everyday activities.

Earphones are typically inserted in front of the ear canal, where they are supported on opposite sides by the tragus and anti-tragus. This allows the earphones to generally stay in place while the user perform tasks other than exercising. However, if the user does exercise and begins to perspire, sweat lubricates the earphones, which can muffle the sound and cause the speakers to cease working. Sweat also drips into the lower part of the ear, known as the intertragic notch, where it pools and keeps the earphones wet with sweat. This reduces the friction between the earphones and the inner ear, which can cause the earphones to slide out of the ear with the slightest of movement.

A temporary solution is to absorb the sweat from the earphones and ear with a dry towel or clothing. However, this is difficult to do, if a dry towel is not readily available or if the user's clothes are already soaked with sweat. Even if the user does dry the earphones, it is usually just a matter of time before the earphones become lubricated again with sweat and fall out of the ear. This inconvenience may prevent some users from wearing earphones while exercising.

There are a number of earphones on the market that claim to be sweat resistant. Despite these claims, these earphones often slip out of the ear when they become lubricated with sweat. U.S. Pat. Publication No. 2013/0327087 describes a necklace to which wires from an earphones are attached. When the earphones slide out of the user's ear, the wires remain connected to the necklace. However, this does not prevent the earphones from falling out of the user's ear in the first place.

U.S. Pat. Publication No. 2014/0211959 integrates earphones into a larger headphone device. However, this defeats the advantage of having earphones that are compact, lightweight, inexpensive and discreet.

U.S. Pat. No. 8,638,970 describes a device with a series of ribs to assist in holding the earphones to the inner ear. However, the friction between these ribs and the ear is reduced when they become lubricated with sweat, which may allow them to slip out of the ear. Also, the ribs of does nothing to prevent sweat from accumulating in the first place.

Accordingly, a need exists for a device that will allow a user to continuously listen to music while sweating without the interruption of having his earphones fall out of his ears.

SUMMARY OF THE INVENTION

The purpose of the inventive subject matter is to accomplish at least one of the following objectives. One objective is to prevent sweat from accumulating in the inner ear. Another objective is to remove sweat that accumulates in the inner ear. A further objective is to prevent a sweat soaked earphone from falling out of the ear. A further objective is to provide a device capable of accomplishing at least one of the foregoing objectives that is small, lightweight, inexpensive, and/or discreet.

The invention is directed towards a device for preventing or removing sweat from the inner ear by allowing a vacuum to occur in tubing or a similar component that connects between the vicinity of the inner ear and the middle section of a converging-diverging nozzle, referred to herein as a nozzle. One end of the tubing is u-shaped, so that it vacuums sweat from the bottom of the inner lower ear through the u-shaped bend and into the tee connection in the middle of the nozzle. The horizontal portion of the tee connection is aligned with the center axis of the nozzle, while the vertical portion of the tee connection is orientated upwards and towards the ear where it connects to the u-shaped tubing.

The converging-diverging nozzle by design has a larger cross-sectional area at both ends, and a smaller cross-sectional area in the middle. When wind blows into the front of the nozzle, or when a user moves forward, air travels into the larger cross-sectional area of the nozzle and continues to travel through the nozzle toward the smaller cross-sectional area in the middle of the nozzle. In doing so, the air velocity accelerates as the cross-sectional area of the nozzle reduces in size. This is in accordance with the continuity equation, which states that in any steady state process, the rate at which mass enters a system is equal to the rate at which mass leaves the system. In other words, to maintain a constant volumetric flow rate through the nozzle, the air travels at a slower speed when it enters the larger cross-sectional area at the end of the nozzle, speeds up as it travels through the smaller cross-sectional area in the middle of the nozzle, and then slows down again as it exits the larger cross-sectional area at the other end of the nozzle.

As the air velocity increases through the smaller cross-sectional area in the middle of the nozzle, the pressure drops in accordance with Bernoulli's Principle, which states that an increase in the speed of a fluid occurs simultaneously with a decrease in pressure. In the inventive subject matter, the decrease in pressure occurs in the middle of the nozzle, which creates a vacuum in the connecting tubing and in the lower part of the ear in the vicinity of the intertragic notch. This vacuum draws sweat from under the earphones at the bottom of the inner ear, and directs it towards the middle of the nozzle. In this way, sweat is removed from the user's ear.

The device of the present embodiment is preferably about two-inches long. The ends of the nozzle are preferably ½-inch in diameter. The middle of the nozzle is preferably ¼-inch in diameter. The connecting tubing from the nozzle to the ear is also preferably ¼-inch in diameter. A device with these dimensions is capable of lifting sweat approximately ½-inch when the user is running about 7 minutes and 30 seconds per mile or 8 miles per hour (mph). The device will also operate with other dimensions, if the cross-sectional areas at the ends of the nozzle are correctly proportioned to the middle cross-sectional area, if the entering air velocity is fast enough. When wind enters the device at an air velocity of approximately 8 mph or greater, the device will vacuum sweat from the inner ear through the tubing that connects to the tee in the middle section of the nozzle. The device can create a greater vacuum if the user moves forward faster, or if wind enters the nozzle at a faster velocity, or if a fan is combined with the nozzle to increase the air velocity.

The device of the present embodiment can be made by connecting two cones horizontally to opposite ends of a tee connection, where the remaining intersecting leg of the tee connection is oriented vertically upwards. One end of tubing can then be connected to the vertically upwards leg of the tee connection, and the other end of the tubing connects to the bottom of the inner ear. The device can be either connected to the earphones itself or to another object, such as a hair clip, a hat, a helmet, ear muffs, eyeglasses, sunglasses, or similar objects.

Another object of the present inventive subject matter is to attach the device to an area below the user's ear, when performing any activity that may generate sweat or when water is present to remove moisture from the ear of the user. For example, the device may be attached to a bicycle helmet to remove sweat from a user's ear while cycling.

Another object of the present inventive subject matter is to incorporate a fan into the device to further increase the air velocity and the resulting vacuum.

For purposes of summarizing the inventive subject matter and the advantages achieved over the prior art, certain configurations of positioning the device below the user's ear, and possible activities it could be used for, have been described herein above. Of course, it is to be understood that the present inventive subject matter can be connected to a user's ear area using a wide variety of connecting mechanisms and worn during a wide variety of activities. Those skilled in the art will also recognize that the inventive subject matter may be positioned on other parts of the user's body or equipment in a manner that achieves or optimizes the purpose of vacuuming sweat or moisture from the inner ear as taught herein without necessarily being worn with earphones or other objects as may be taught or suggested herein.

All of these embodiments are intended to be within the scope of the inventive subject matter herein disclosed. These and other embodiments of the present inventive subject matter will become readily apparent to those skilled in the art from the following detailed description of the preferred embodiments having reference to the attached figures, the inventive subject matter not being limited to any particular preferred embodiments disclosed.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
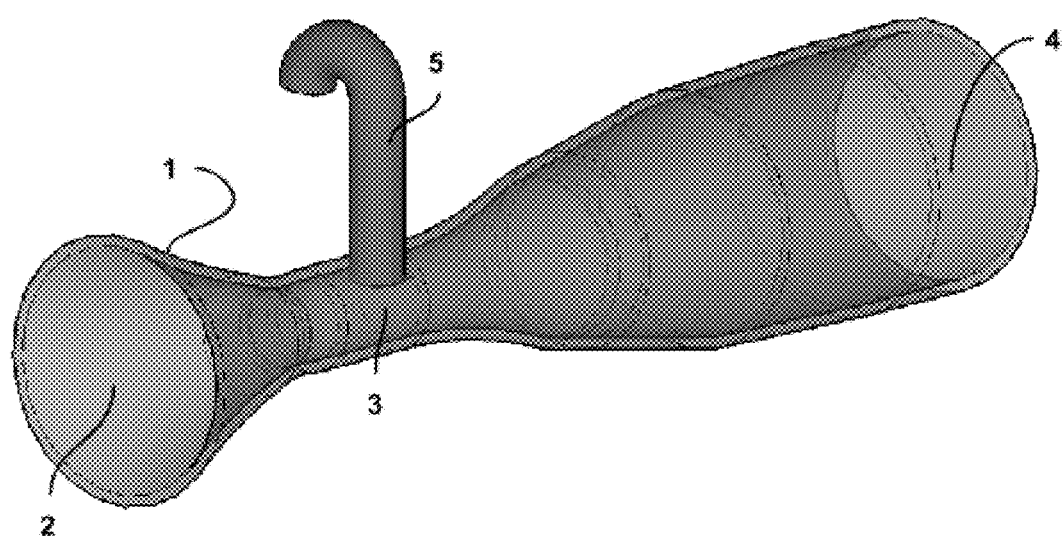
FIG. 1 is an isometric view of the device in which the invention is implemented.
Figure 2:
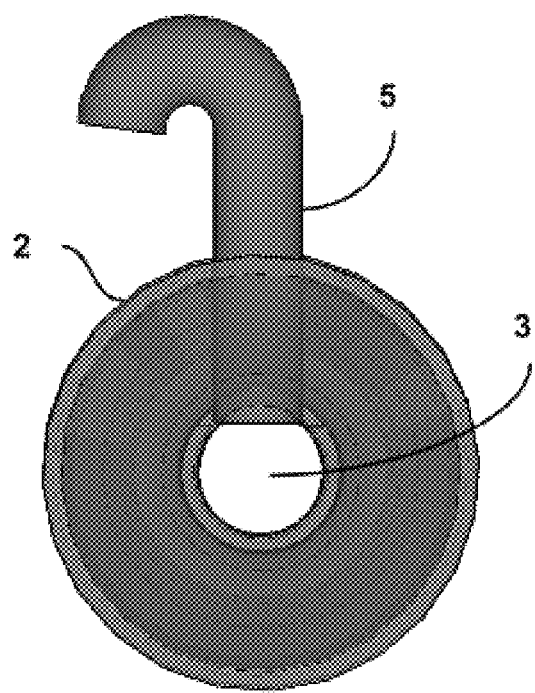
FIG. 2 is an end view of the device in which the invention is implemented of FIG. 1.
Figure 3:
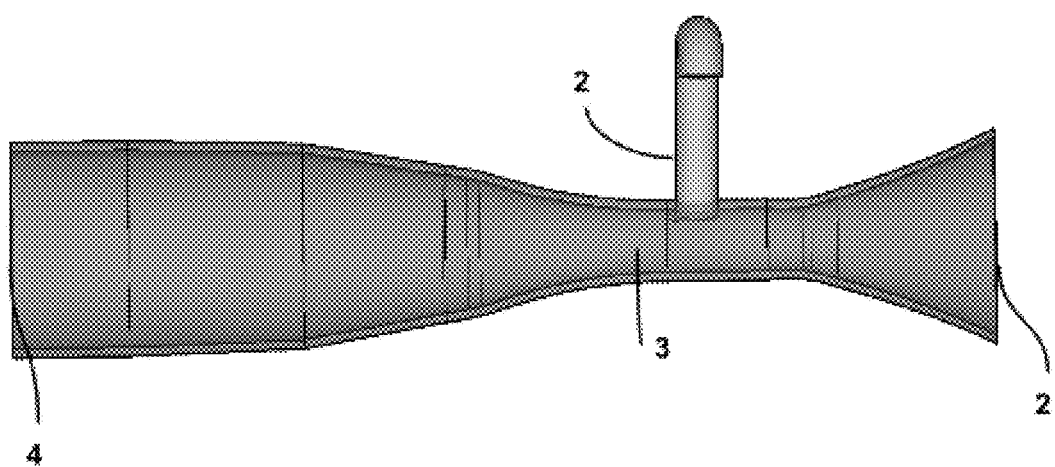
FIG. 3 is a side view of the device in which the invention is implemented of FIG. 1.
Figure 4:
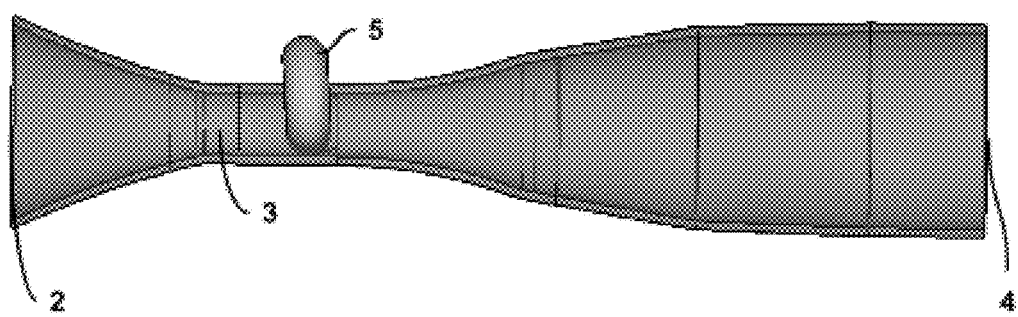
FIG. 4 is a top view of the device in which the invention is implemented of FIG. 1.

The following is a detailed description of the figures in the present inventive subject matter. The figures are illustrative of an embodiment, but are not to be construed as restrictive as to the entirely conceived inventive subject matter. It is also to be understood that this inventive subject matter is not limited to any particular embodiments described, as such may, of course, vary. It is also to be understood that the terminology used herein is for the purpose of describing particular embodiments only, and is not intended to be limiting, since the scope of this inventive subject matter will be limited only by the appended claims. The contents of all reference(s), patent(s), and patent application publication(s) cited in this application are hereby incorporated by reference in their entireties. In the following detailed description, numerous specific details are set forth in order to explain and provide a thorough understanding of the present inventive subject matter. However, it is apparent that the present inventive subject matter may be practiced without these specific details.

Referring now in more detail to FIGS. 1-4, there are shown a device 1 for removing sweat or moisture from the inner ear, having an entering outside cross-sectional area 2, a smaller middle cross-sectional area 3, and an exiting outside cross-sectional area 4. Air enters the device through the outside cross-sectional area 2 and accelerates as the cross-sectional area decreases toward the smaller middle cross-sectional area 3. The air travels at a faster velocity through the smaller middle cross-sectional area 3 to maintain a constant volumetric flow rate through the nozzle. As the air velocity increases, the pressure drops in the middle of the nozzle in accordance with Bernoulli's Principle. The air then decelerates as it continues to travel from the middle of the nozzle 3 toward the larger end cross-sectional area 4.

Figure 5:
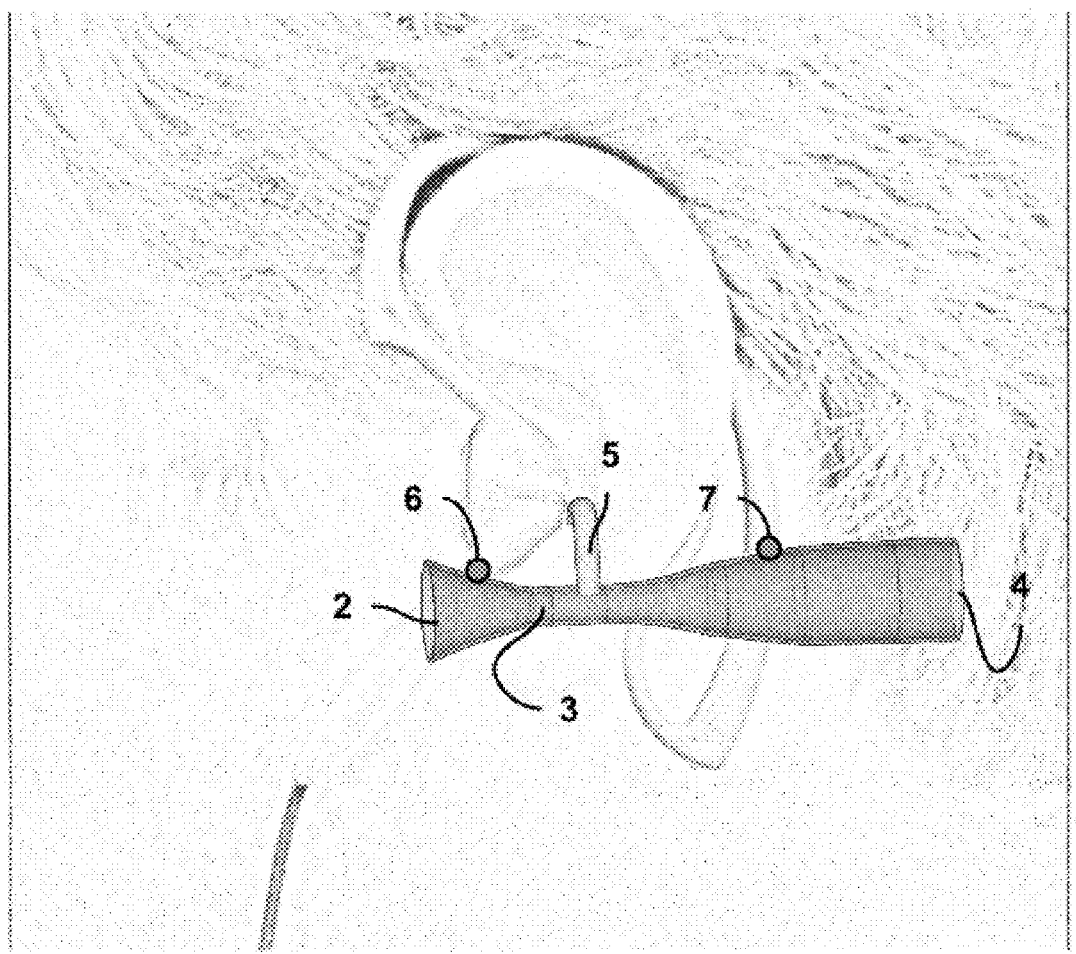
FIG. 5 is a side view of the device in which the invention is implemented of FIG. 1, where it attaches to an earphone and an earphone hook, which is secured to the user's left ear. Similarly, the device can be attached to the user's right ear.

FIG. 5 is a side view of the device with an attachment 6 that connects one end of the device to the stem of the earphone and an attachment 7 that connects the other end to a hook or hanger of the earphone that extends over the user's ear. One end of the tubing 5 is u-shape, so that it vacuums sweat from the bottom of the inner lower ear. The other end of the tubing 5 connects to a tee connection 3 in the middle of the nozzle. The horizontal portion of the tee connection is aligned with the center axis of the nozzle, while the vertical portion of the tee connection is orientated upwards toward the ear.

The device can also be secured to or integrated into a user's hair clip, hat, helmet, ear muffs, eyeglasses, sunglasses, or other object connected to the user's body. Additionally, a fan can be incorporate into the device to further increase the air velocity and the resulting vacuum. This may help those, who run at a speed that is too slow to create the necessary vacuum to remove sweat from the inner ear.

Device 1 is preferably a converging-diverging nozzle that is approximately 2 inches in length, having larger cross-sectional areas at each end 2, 4 as compared to the middle section 3. However, all suitable converging-diverging nozzle are contemplated. For example, the converging-diverging nozzle may have any appropriate length from 0.5-inch to 6 inches, depending on the cross-sectional areas of each end 2, 4 and the middle section 3. It is also contemplated that device 1 can have any desired composition, from steel or other very strong materials to relatively soft materials, including wood, plastic, and composites.

Although this inventive subject matter has been disclosed in the context of certain preferred embodiments and examples for removing moisture from the inner ear, it will be understood by those skilled in the art that the present inventive subject matter extends beyond the specifically disclosed embodiments to other alternative embodiments and/or uses and obvious modifications and equivalents thereof. Thus, it is intended that the scope of the present inventive subject matter herein disclosed should not be limited by the particular disclosed embodiments described above, but should be determined only by a fair reading of the claims that follow.

What is claimed:

1. A device for vacuuming sweat from the lower inner earlobe, the device comprising:
   at least one tee connection;
   at least one earphone having at least one speaker with dimensions that allow it to be inserted into the inner part of the outer earlobe in the vicinity of the intertragic notch between the tragus and anti-tragus;
   at least one upside down u-shaped tubing approximately one-quarter inch in diameter, one-inch long, and one-half inch in height having a first and second end, wherein the first end is positioned under the earphone in the inner part of the outer earlobe in the vicinity of the intertragic notch, and the second end is connected to the tee connection;
   at least one a converging-diverging nozzle, said converging-diverging nozzle approximately one-half inch in diameter and two-inches long including a middle section, wherein said middle section comprises a said tee connection and said upside down u-shaped tubing;
   at least one earphone hanger;
   means for connecting together said tee connection, said at least one earphone, said upside down u-shaped tubing, and said converging-diverging nozzle to said earphone hanger;
   means for attaching the earphone hanger to an object selected from the group consisting of an earlobe, hair clip, hat helmet ear muffs, eyeglasses, and sunglasses;
   means for a user wearing the assembled combination of the tee connection, the earphone, the converging-diverging nozzle, the upside down u-shaped tubing, and the earphone hanger;
   wherein when the user is running at a velocity of eight miles per hour or greater, the device:
   receives air into the front end of the converging-diverging nozzle;
   allows the air to increase in velocity as it travels towards the middle section of the converging-diverging nozzle;
   creates a vacuum in the tee connection and the upside down u-shaped tubing; and
   allows sweat from the user to be vacuumed from underneath the earphone in the vicinity of the intertragic notch towards the tee connection where it drips out the back of the nozzle.

2. The device of claim 1, wherein said converging-diverging nozzle further comprising a fan, said fan increasing the air velocity through the converging-diverging nozzle, to allow sweat from the user to be vacuumed from underneath the earphone in the vicinity of the intertragic notch towards the tee connection where it drips out the back of the nozzle when a user is running at a velocity of less than eight miles per hour.

3. A method of using a device for vacuuming sweat from the lower inner earlobe, the method comprising the steps of:
   providing at least one tee connection;
   providing at least one earphone having at least one speaker with dimensions that allow it to be inserted into the inner part of the outer earlobe in the vicinity of the intertragic notch between the tragus and anti-tragus;
   providing at least one upside down u-shaped tubing approximately one-quarter inch in diameter, one-inch long, and one-half inch in height having a first and second end, wherein the first end is positioned under the earphone in the inner part of the outer earlobe in the vicinity of the intertragic notch, and the second end is connected to the tee connection;
   providing at least one converging-diverging nozzle, said converging-diverging nozzle approximately one-half inch in diameter and two-inches long including a middle section, wherein said middle section comprises said tee connection and said upside down u-shaped tubing;
   providing at least one earphone hanger;
   providing means for connecting together said tee connection, said at least one earphone, said upside down u-shaped tubing, and said converging-diverging nozzle to said earphone hanger;
   providing means for attaching the earphone hanger to an object selected from the group consisting of an earlobe, hair clip, hat helmet ear muffs, eyeglasses, and sunglasses;
   providing means for a user wearing the assembled combination of the tee connection, the earphone, the converging-diverging nozzle, the upside down u-shaped tubing, and the earphone hanger;
   wherein when the user is running at a velocity of eight miles per hour or greater, the device:
   receives air into the front end of the converging-diverging nozzle; allows the air to increase in velocity as it travels towards the middle section of the converging-diverging nozzle;
   creates a vacuum in the tee connection and the upside down u-shaped tubing; and allows sweat from the user to be vacuumed from underneath the earphone in the vicinity of the intertragic notch towards the tee connection where it drips out the back of the nozzle.

4. The method of claim 3, wherein said converging-diverging nozzle further comprising a fan, the fan increasing the air velocity through the converging-diverging nozzle.

* * * * *